United States Patent [19]

Evers et al.

[11] 3,961,093
[45] June 1, 1976

[54] NOVEL FLAVORING COMPOSITIONS AND PRODUCTS CONTAINING 2-METHYL-3-THIO-(2-METHYLBUTYRYL)-FURAN

[75] Inventors: William J. Evers, Red Bank; Howard H. Heinsohn, Jr., Hazlet; Bernard J. Mayers, Cliffwood Beach; Elizabeth A. Karoll, Old Bridge, all of N.J.

[73] Assignee: International Flavors & Fragrances Inc., New York, N.Y.

[22] Filed: Aug. 12, 1975

[21] Appl. No.: 603,934

Related U.S. Application Data

[63] Continuation-in-part of Ser. No. 478,369, June 11, 1974, Pat. No. 3,917,869, which is a continuation-in-part of Ser. No. 386,451, Aug. 7, 1973, Pat. No. 3,873,731.

[52] U.S. Cl. .............................................. 426/535
[51] Int. Cl.$^2$ ......................................... A23L 1/226
[58] Field of Search ................. 426/535; 260/347.2, 260/332.2

[56] References Cited
UNITED STATES PATENTS

| | | | |
|---|---|---|---|
| 3,666,495 | 5/1972 | Evers | 426/535 |
| 3,873,731 | 3/1975 | Evers et al. | 426/535 |
| 3,917,869 | 11/1975 | Evers et al. | 426/535 |

FOREIGN PATENTS OR APPLICATIONS 1,283,912    8/1972    United Kingdom

*Primary Examiner*—Joseph M. Golian
*Attorney, Agent, or Firm*—Arthur L. Liberman; Harold Haidt; Franklin D. Wolffe

[57] ABSTRACT

Methods for altering, modifying or enhancing the roasted, nutty taste and aroma of foodstuffs comprising incorporating with such foodstuffs a small but effective amount of 2-methyl-3-thio-(2-methylbutyryl)-furan having the formula:

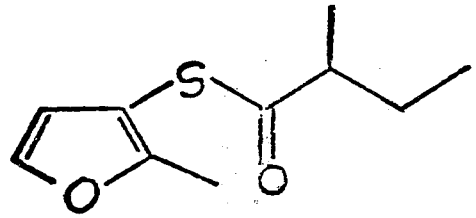

together with compositions containing the 2-methyl-3-thio-(2-methylbutyryl)-furan for use in altering, modifying or enhancing such organoleptic properties.

2 Claims, No Drawings

NOVEL FLAVORING COMPOSITIONS AND PRODUCTS CONTAINING 2-METHYL-3-THIO-(2-METHYLBUTYRYL)-FURAN

This application is a continuation-in-part of application for U.S. Letters Pat. No. 478,369 filed on June 11, 1974 now U.S. Pat. No. 3,917,869, issued on Nov. 4, 1975 which, in turn is a continuation-in-part of U.S. application for Letters Patent Ser. No. 386,451 filed on Aug. 7, 1973 now U.S. Pat. No. 3,873,731, issued on Mar. 25, 1975.

BACKGROUND OF THE INVENTION

The present invention relates to altering, modifying or enhancing the aroma or taste of a foodstuff. More particularly, this invention is concerned with the use of 2-methyl-3-thio-(2-methylbutyryl)-furan to alter, modify or enhance the flavor and/or aroma characteristics of a foodstuff.

The terms "alter" and "modify" in these various forms are used herein to mean the supplying or imparting of a flavor or aroma characteristic or note to an otherwise bland, relatively tasteless or non-odorous substance, or augmenting an existing flavor or aroma characteristic where the natural flavor or intrinsic odor is deficient in some regard, or supplementing the existing flavor or aroma impression to modify its quality, character, taste or aroma.

The term "enhance" as used herein is inended to mean the intensification of specific flavor or aroma character, note or nuance already presented in the overall organoleptic impression of a foodstuff or flavor formulation without causing a change in kind to occur with respect to the quality of the said flavor or aroma character, note or nuance.

The term "foodstuff" as used herein includes both solid and liquid ingestible materials which usually do, but need not have nutritional value. Thus, foodstuffs include meats, gravies, soups, convenience foods, beverages, dairy products, candies, vegetables, cereals, soft drinks, snacks and the like.

Artificial flavoring agents for foodstuffs have received increasing attention in recent years. In many areas, such food flavoring agents are preferred over natural flavoring agents at least in part because of the uniform flavor that may be so obtained. For example, natural food flavoring agents such as extracts, essences, concentrates and the like are often subject to wide variation due to changes in the quality, type and treatment of the raw materials. Such variation can be reflected in the end product and results in unreliable flavor characteristics and uncertainty as to consumer acceptance and cost. Additionally the presence of the natural product in the ultimate food may be undesirable because of increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in peparing artificial flavoring agents is that of achieving as nearly as possible a true flavor reproduction. This generally proves to be a difficult task since the magnetism for flavor development in many foods is not understood. This is notable in products having roasted, nutty or hazelnut-like flavor characteristics.

Reproduction of roasted, nutty and hazelnut-like flavors and aromas has been the subject of the long and continuing search by those engaged in the production of foodstuffs, since such flavors and anemas find use in such substances as meat gravies and protein containing food supplements. The severe shortage of foods, especially protein foods, in many parts of the world has given rise to the need for utilizing non-meat sources of proteins and making such proteins as palatable and as meat-like as possible. Hence, materials which will closely simulate or exactly reproduce the flavor and aroma of roasted meat products or roasted nut-like tasting products are required.

PRIOR ART

Various 2-acetyl furans and 2-acetyl thiophenes have been suggested for use in coffee flavors. British Pat. No. 1,156,481 shows 2-acetyl furan and 2-acetyl-5-methyl furan as flavoring agents for coffee. British Pat. No. 1,156,481 discloses 2-acetyl thiophene and various monoalkyl-2-acetyl thiophenes as flavoring agents for coffee. Schultz, Day and Libbey, The Chemistry and Physiology of Flavors. The AVI Publishing Company Inc., (1967), pages 442 and 443 disclose that 2-acetyl furan, 2-acetyl thiophene and 5-methyl-2-acetyl furan are among the volatile constituents of coffee. Arctander, Perfume and Flavor Chemicals. Vol. 1, Item 39, Montclair, N.J. (1969) states that 2-acetyl furan could find use in floral fragrances. And, Dutch Published Application 68.12899 shows that 2-acetyl-3-methyl furan and 2-propionyl-3-methyl furan give a roast bean note to coffee.

South African Pat. No. 69/4539 dated June 26, 1969 discloses, for use as intermediates for subsequent reaction with hydrogen sulfide to form flavor compounds, dihydro furyl thioesters having the structure:

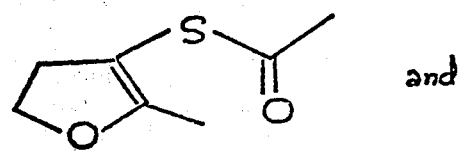

and

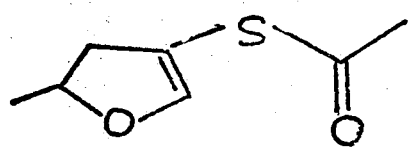

See pages 6 and 7 of the said South African Patent.

Volume 24 "Food Technology" page 535 (May, 1970) [the "Gras IV" list No. 3162] discloses the use as a flavor adjuvant furfural S thioacetate having the structure:

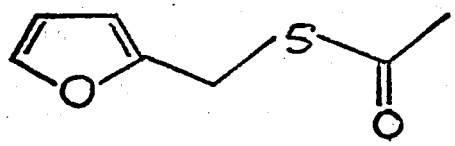

Nothing in the prior art, however, sets forth implicitly or explicitly the 3-furyl thioester of our invention and their unique and advantageous and unobvious flavor properties.

SUMMARY OF THE INVENTION

In accordance with this invention, it has been found that 2-methyl-3-thio-(2-methylbutyryl)-furan having the structure:

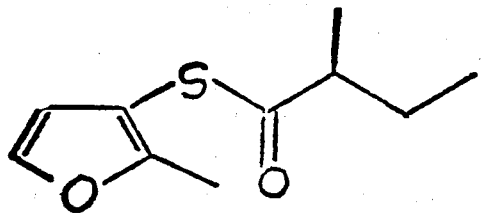

is used to alter, modify or enhance the roasted, nutty or hazelnut flavor or aroma of a foodstuff.

DESCRIPTION OF THE PREFERRED EMBODIMENTS

It has been found that the 2-methyl-3-thio-(2-methylbutyryl)-furan of this invention is useful in nut flavors, especially hazelnut and walnut, vanilla and milk chocolate flavors, caramel and coffee flavors. It also adds desired nuances to gravy and meat flavors. It may be used in almond, marzipan, cherry, and baked goods, and fruit flavors such as grape.

Admixtures of the 2-methyl-3-thio-(2-methylbutyryl)-furan and with other flavoring or aromatizing materials offers the advantages of combining the beneficial and organoleptic qualities of each of the compounds into a total impact which is superior to or different from the characteristics of the sole ingredient. For example, salt enhances the meat gravy character of the 2-methyl-3-thio-(2-methylbutyryl)-furan and sugar enhancs the sweet dried hazelnut, coffee caramel notes. The formulator can simulate a wide variety of organoleptic characteristics to evoke a predetermined taste response on the part of the consumer.

Generally in use the 2-methyl-3-thio(-b 2-methylbutyryl)-furan is admixed with one or more auxiliary flavoring adjuvants. The precise adjuvants employed will depend upon the ultimate use contemplated and the organoleptic character desired. Flavoring adjuvants are recognized in the art and are ingestibly acceptable or non-toxic. Such flavoring adjuvants include stabilizers, thickeners, surface active agents, conditioners, flavorants and flavor intensifiers.

Stabilizers include preservatives, e.g., sodium chloride, antioxidants, e.g., calcium sodium ascorbate, ascorbic acid, butylated hydroxyanisole (mixture of 2 and 3 tertiary butyl-4-hydroxyanisole), butylated hydroxy toluene (2,6di-tertiarybutyl-4-methyl phenol), propyl gallate and the like, sequestrants, e.g., citric acid.

Thickeners include carriers, binders, protective colloids, suspending agents, emulsifiers and the like, e.g., agar-agar, cerrageenan; cellulose and cellulose derivatives such as carboxymetyl cellulose and methyl cellulose; natural and synthetic gums such as gum arabic, gum tragacanth; gelatin, proteinaceous materials; lipids; carbohydrates; starches; pectins, and emulsifiers, e.g. mono- and di-glycerides of fatty acids.

Surface active agents include emulsifying agents, e.g. fatty acids such as capric acid, caprylic acid, palmitic acid, myristic acid and the like, mono- and di-glycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g. benzoyl peroxide, calcium peroxide, hydrogen peroxide and the like; starch modifiers such as peracetic acid, sodium chlorite, sodium hypochlorite; propylene oxide, succinic anhydride and the like, buffers and neutralizing agents, e.g. sodium acetate, ammonium bicarbonate, ammonium phosphate, citric acid, lactic acid, vinegar and the like; colorants, e.g., carminic acid, cochineal, tumeric and curcumin and the like; firming agents such as aluminum sodium sulfate, calcium chloride and calcium gluconate; texturizers; anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferric pyrophosphate, ferrous gluconate and the like, riboflavin, vitamins, zinc sources such as zinc chloride, zinc sulfate and the like.

Flavorants and flavor intensifiers include organic acids, e.g., fatty saturated, unsaturated and amino acids; alcohols, e.g. primary and secondary alcohols; esters, carbonyl compounds including aldehydes and ketones, lactones; cyclic organic material including benzene derivatives; alicyclics, heterocyclics such as furans, particularly 2-acetylfuran, pyridines, pyrazines and the like, sulfur-containing materials including thiazoles, thiols, sulfides, disulfides and the like; so-called flavor potentiators such as monosodium glutamate, guanylates, inosinates, natural and synthetic flavorants such as vanillin, natural gums and the like; spices, herbs, essential oils and extractives including anise, anise oil, akanet root extract, bay leaves, capsicum extract and the like.

The specific flavoring adjuvant selected for use may be either solid or liquid, depending upon the desired physical form of the ultimate product, i.e., foodstuff, whether simulated or natural, and should, in any event, be capable of providing an environment in which the 2-methyl-3-thio-(2-methylbutyryl)-furan can be dispersed or admixed to provide a homogeneous medium without undergoing any additional reaction and without detracting from the organoleptic characteristics provided by the 2-methyl-3-thio-(2-methylbutyryl)-furan. In addition, selection of one or more flavoring adjuvants as well as the quantities thereof will depend upon the precise organoleptic character desired in the finished product; thus, in the case of flavoring compositions, ingredient selection will vary in accordance with the foodstuff to which the flavor and aroma are to be imparted. In contra-distinction, in the preparation of solid products, e.g., simulated foodstuffs, ingredients capable of providing normally solid compositions should be selected such as various cellulose derivatives.

The flavoring ingredients can be added to the consumable material to be flavored at any convenient point in the production of the finished product. They can be added in the original mixture, dough, emulsion batter or at any time in the cooking operation. Alternatively, they can be added at a later stage of processing if volatilization losses would be excessive during earlier processing.

Among the preferred flavoring or aromatizing adjuvants are vanillin, benzaldehyde, methyl furoate, diacetyl, maltol, methyl cyclopentenolone, pyruvic acid, isoamyl levulinate, ethyl anthranilate, ethyl acetate, orange oil, dimethyl anthranilate, ethyl heptanoate, acetoin, butyl butyryl lactate, ethyl vanillin, ethyl butyrate, rose oil, benzyl acetate, tolyl aldehyde, alpha ionone, para-tolylacetaldehyde, heliotropin, methyl thiazole alcohol (4-methyl-5-β-hydroxyethyl thiazole), 2-methyl butanethiol, 4-mercapto2-butanone, 3-mercapto-4-pentanone, 1-mercapto-2-propanone, benzaldehyde, furfural, furfural alcohol, 2-mercapto propionic acid, 2-pentene, alkyl pyrazine, methyl pyrazine, 2-ethyl-3-methyl pyrazine, tetramethyl pyrazine, polysulfides, dipropyl disulfide, methyl benzyl disulfide, alkyl thiophenes, 2-butyl thiophene, 2,3-dimethyl thiophene, 5-methyl furfural, acetyl furan, 2,4-decadienal, guiacol, phenyl acetaldehyde, δ-decalactone, d-limonene, acetoin, amyl acetate, maltol, ethyl butyrate, levulinic acid, piperonal, ethyl acetate, n-octanal, n-pentanal, hexanal, diacetyl, monosodium glutamate, sulfur-containing amino acids, cysteine, hydrolyzed vegetable protein, hydrolyzed fish protein, and tetramethyl pyrazine.

The amount of the 2-methyl-3-thio-(2-methylbutyryl)-furan employed in a particular instance can vary over a relatively wide range to achieve the desired organoleptic effects and in accordance with the ultimate consumer use. Thus, correspondingly greater amounts would be necessary in those instances wherein the ultimate foodstuff to be flavored or aromatized is relatively bland to the senses; whereas, relatively lesser quantities may suffice for purposes of enhancing a composition merely deficient in a natural flavor or aroma. The primary requirement is that the amount selected be effective, i.e., sufficient to alter the organoleptic characteristics of the foodstuff to which it is added or incorporated. The quantity used will depend upon the ultimate consumable product, the amount and type of flavor or aroma initially present in the product, required and other preference factors, storage conditions, and the preconsumption or processing conditions to which the product or composition will be subject.

Effective quantities of the 2-methyl-3-thio-(2-methylbutyryl)-furan of this invention range from 0.1 parts per billion to about 35 parts per million based on the total weight of the foodstuff to which it is added. While larger concentrations can be used they are less economical since additional amounts do not necessarily give equivalent incremental flavor enhancement. In those instances wherein the 2-methyl-3-thio-(2-methylbutyryl)-furan of this invention is added to the foodstuff as an essential and integral part of a flavoring composition, it is, of course, necessary that the total quantity of flavoring composition employed be sufficient to yield an effective concentration.

Flavoring compositions prepared in accordance with the present invention preferably contain the 2-methyl-3-thio-(2-methylbutyryl)-furan in concentrations ranging from $5 \times 10^{-8}$ to about 10% by weight, based on the total weight of said flavoring compositions, but may contain as much as 80 or 90% by weight of the 2-methyl-3-thio-(2-methylbutyryl)-furan if the flavoring composition is then applied in very small amount.

All parts, proportions, percentages and ratios herein are by weight unless otherwise indicated.

The following examples are given to illustrate embodiments of the invention as it is now preferred to practice it. It will be understood that these examples are illustrative, and the invention is not to be considered as restricted thereto except as indicated in the appended claims.

EXAMPLE I

PREPARATION OF 2-METHYL-3-THIO-(2-METHYLBUTYRYL-FURAN

Into a 500 ml flask equipped with stirrer, thermometer, reflux condenser and addition funnel is added, 29 g of 2-methyl-3-furanthiol (0.255 moles) dissolved in 200 ml of diethyl ether. 30.5 g of 2-methyl-butyryl chloride (0.255 moles) dissolved in 100 ml of diethyl ether is then added to the addition funnel. The 2-methylbutyrl chloride solution is then added to the reaction mass, dropwise, over a period of 15 minutes from the addition funnel. 20.2 g of pyridine (0.255 moles) is then added to the reaction mass and the stirring is continued for another 10 minutes. When addition is complete, the reaction mass is stirred for a period of 80 minutes, after which it is allowed to remain, for a period of 72 hours, at room temperature.

The reaction mass is then poured into 500 ml of water yielding two phases; an aqueous phase having pyridine hydrochloride dissolved therein, and an ether layer. The ether layer is washed with 500 ml of 4% hydrochloric acid and 500 ml of saturated sodium bicarbonate solution. The ether layer is then dried over anhydrous sodium sulfate and concentrated to 39.1 g of a yellow oil, whic is crude 2-methyl-3-thio-(2-methylbutyryl)-furan. This crude material is then distilled at a temperature of 65°–66°C and a pressure of 0.55 mm Hg, yielding 32.7 g of 2-methyl-3-thio-(2-methylbutyryl)-furan having the structure:

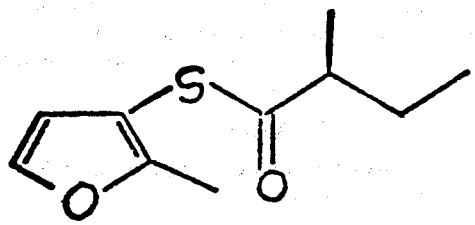

Mass Spectral Analysis

Molecular Ion, then in descending intensity: 198, 57, 85, 86, 41, 43, 114, 39 m/e NMR Spectrum (CDCl$_3$)

| | |
|---|---|
| 7.38 | (d,1,J=1.8 Hz) |
| 6.32 | (d,1,J=1.8 Hz) |
| 2.68 | (m,1) |
| 2.26 | (s,3) |
| 1.67 | (m,2) |
| 1.21 | (d,3) |
| 0.96 | (t,3) ppm |

EXAMPLE II

The following formulation is prepared:

| Ingredient | Parts by Weight |
|---|---|
| Liquid hydrolyzed vegetable protein | 90 |
| 4-Methyl-beta-hydroxy-ethyl-thiazole | 5 |

-continued

| Ingredient | Parts by Weight |
| --- | --- |
| Tetrahydro thiophene-3-one | 1 |
| Furfuryl mercaptan | 0.01 |
| 2-Nonenal | 0.50 |
| Difurfuryl disulfide | .49 |
| Dimethyl sulfide | 0.50 |
| Methyl mercaptan | 0.50 |
| 2-Methyl-3-thio-(2-methylbutyryl)-furan | 2.00 |

The 2-methyl-3-thio(2-methylbutyryl)-furan causes the above formulation to be distinctly roast meat in character and in aroma and taste and with a sweet nuance causes it to be typically gravy-like (sweet roast meat gravy). The 2-methyl-3-thio-(2-methylbutyryl)-furan is stronger and consequently the flavor is more predominantly sweet roast meat. The sweet and roasted notes are very reminiscent of roast meat gravy.

EXAMPLE III

A walnut flavor formulation is prepared by blending the following ingredients:

| Ingredients | Parts by Weight |
| --- | --- |
| Vanillin | 4.0 |
| Ethyl-2-methyl butyrate | 1.0 |
| Butyl isovalerate | 4.0 |
| 2,3-Diethyl pyrazine | 0.5 |
| Methyl cyclopentenolone | 8.0 |
| alpha-hydroxy-beta-methyl-$\Delta\alpha\beta$-$\gamma$-hexenolactone | 2.0 |
| benzaldehyde | 6.0 |
| valerian oil Indonesia (0.1% solution in propylene glycol) | 0.5 |
| propylene glycol | 74.0 |

This walnut flavor is compared in water at the rate of 10 ppm with the identical flavor to which 0.5 parts of 2-methyl-3-thio-(2-methylbutyryl)-furan is added. The flavor containing 2-methyl-3-thio-(2-methylbutyryl)-furan has a fuller, more natural walnut kernel like taste because of the addition to the formulation of said thiophene compound.

EXAMPLE IV

A vanilla flavor formulation is prepared by blending the following ingredients:

| Ingredients | Parts by Weight |
| --- | --- |
| Maltol | 2.0 |
| Ethyl Vanillin | 5.0 |
| Vanillin | 18.0 |
| 1,2 Benzodihydropyrone 10% (ethanol 95%) | 1.0 |
| Anisaldehyde (1% solution in ethanol 95%) | 0.5 |
| Balsam Peru (1% solution in ethanol 95%) | 1.5 |
| Ethyl alcohol | 72.0 |

This vanilla flavor is compared with the same flavor to which 0.01% 2-methyl-3-thio-(2-methylbutyryl)-furan is added. The flavors are compared at the rate of 0.02% or 200 ppm in water. The sample containing 2-methyl-3-thio-(2-methylbutyryl)-furan has more of the natural sweetness as reproduced by natural vanilla extract, and also has a fuller taste and better mouthfeel.

EXAMPLE V

A walnut flavor is prepared by blending the following ingredients:

| Ingredients | Parts by Weight |
| --- | --- |
| Vanillin | 4.0 |
| Ethyl-2-methylbutyrate | 1.0 |
| Butyl/isovalerate | 4.0 |
| 2,3-diethyl pyrazine | 0.5 |
| Methyl cyclopentenolone | 8.0 |
| Alpha-hydroxy-beta-methyl-$\Delta$ alpha, beta- $\gamma$ -hexenolactone | 2.0 |
| Benzaldehyde | 6.0 |
| Valerian Oil Indonesian (0.1% solution in propylene glycol) | 0.5 |
| Propylene glycol | 74.0 |

This walnut flavor is compared in water at the rate of 10 ppm with the same flavor to which 2% 2-methyl-3-thio-(2-methylbutyryl)-furan is added. The flavor containing the 2-methyl-3-thio-(2-methylbutyryl)-furan has a sweeter, more walnut kernel and rounded taste and is therefore improved.

What is claimed is:

1. A process for altering modifying or enhancing the roasted, nutty or hazelnut flavor of a foodstuff which comprises adding thereto 2-methyl-3-thio-(2-methylbutyryl)-furan having the structure:

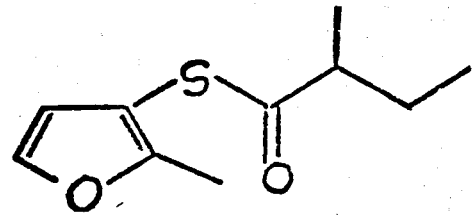

in an amount of from 0.1 parts per billion to about 35 parts per million based on the total weight of the foodstuff.

2. A composition adapted to alter modify or enhance the roasted, nutty taste and aroma of a foodstuff which comprises (i) 2-methyl-3-thio-(2-methylbutyryl)-furan having the structure:

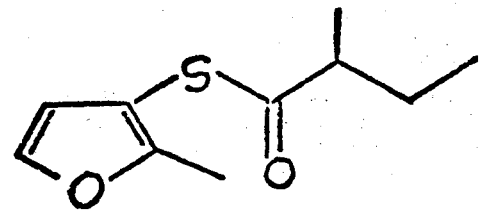

in a concentration ranging from $5 \times 10^{-8}$ to 90% by weight based on the total weight of said flavoring compositions and (ii) an adjuvant material organoleptically compatible and non-reactive with said 2-methyl-3-thio-(2-methylbutyryl)-furan selected from the group consisting of:

Methyl thiazole alcohol;
2-Methyl butanethiol;
4-Mercapto-2-butanone;
3-Mercapto-4-pentanone;
1-Mercapto-2-propanone;
Benzaldehyde;
Furfural;
Furfural Alcohol;
2-Mercapto propionic acid;
2-Pentene;
Alkyl pyrazine;

Methyl pyrazine;
2-Ethyl-3-methyl pyrazine;
Tetramethyl pyrazine;
Polysulfides;
Dipropyl disulfide;
Methyl benzyl disulfide;
Alkyl thiaphenes;
2-Butyl thiaphene;
2,3-Dimethyl thiaphene;
5-Methyl furfural;
Acetyl furan;
2,4-Decadienal;
Guiacol;
Phenyl acetaldehyde;
δ -Decalactone;
d-Limonene;
Acetoin;
Amyl acetate;
Maltol;
Ethyl butyrate;
Levulinic acid;
Piperonal;
Ethyl acetate;
n-Octanal;
n-Pentanal;
Hexanal;
Diacetyl;
Monosodium glutamate;
Sulfur-containing amino acids;
Cysteine;
Hydrolyzed vegetable protein;
Hydrolyzed fish protein;
Tetramethylpyrazine;
Vanillin;
Benzaldehyde;
Methyl Furoate;
Diacetyl;
Maltol;
Methyl cyclopentenolone; Pyruvic acid;
Isoamyl levulinate;
Ethyl anthranilate;
Ethyl acetate;
Orange oil;
Dimethyl anthranilate;
Ethyl heptanoate;
Acetoin;
Butyl butyryl lactate;
Ethyl vanillin;
Ethyl butyrate;
Rose oil;
Benzyl Acetate;
Tolyl Aldehyde;
Alpha ionone;
Para-tolylacetaldehyde; and
Heliotropin

\* \* \* \* \*

UNITED STATES PATENT AND TRADEMARK OFFICE
CERTIFICATE OF CORRECTION

PATENT NO. : 3,961,093
DATED : June 1, 1976
INVENTOR(S) : William J. Evers; Howard H. Heinsohn, Jr.; Bernard J. Mayers; Elizabeth A. Karoll It is certified that error appears in the above—identified patent and that said Letters Patent are hereby corrected as shown below:

Col. 1, line 31, next to last word, "inended" should be --- intended ---

Col. 1, line 64, "peparing" should be --- preparing ---

Col. 3, line 45, last half of line "2-methyl-3-thio(-b methyl-" should be --- 2-methyl-3-thio-2-methyl- ---

Col. 3, line 58, "(2,6di-" should be --- (2,6-di- ---

Col. 3, line 63, "cerrageenan;" should be --- carrageenan; ---

Col. 5, line 10, "4-mercapto2-butanone" should be --- 4-mercapto-2-butanone ---

Col. 6, line 10, title of example, "(2-METHYLBUTYRYL-" should be --- (2-METHYLBUTYRYL)- ---

Col. 6, line 19, first word, "methylbutyrl" should be --- methylbutyryl ---

Col. 6, line 34, fourth word, "whic" should be --- which ---

Signed and Sealed this

Twenty-eighth Day of September 1976

[SEAL]

Attest:

RUTH C. MASON
*Attesting Officer*

C. MARSHALL DANN
*Commissioner of Patents and Trademarks*